United States Patent [19]

Stormby

[11] Patent Number: 4,759,376
[45] Date of Patent: Jul. 26, 1988

[54] ENDOCERVICAL SAMPLING BRUSH AND SMEAR METHOD

[76] Inventor: Nils Stormby, Stadiongatan 65, 20074 Malmo 20, Sweden

[21] Appl. No.: 38,947

[22] Filed: Apr. 16, 1987

Related U.S. Application Data

[63] Continuation of Ser. No. 815,766, Jan. 2, 1986, abandoned, which is a continuation of Ser. No. 614,487, May 29, 1984, abandoned.

[51] Int. Cl.[4] .............................................. A61B 10/00
[52] U.S. Cl. ..................................... 128/756; 128/304; 15/206
[58] Field of Search .................. 128/756, 304; 15/206, 15/159 A

[56] References Cited

U.S. PATENT DOCUMENTS

| | | | |
|---|---|---|---|
| 3,776,219 | 12/1973 | Brown | 128/304 |
| 3,881,464 | 5/1975 | Levene | 128/756 |
| 4,108,162 | 8/1978 | Chikaswigg et al. | 128/756 |
| 4,127,113 | 11/1978 | Nollan | 128/756 |
| 4,227,537 | 10/1980 | Suciu et al. | 128/756 |
| 4,395,943 | 8/1983 | Basnoli | 15/206 |

OTHER PUBLICATIONS

"Mill-Rose Disposable Cytology Brushes", 2/1979.
Acta Obstetricia et Gynecologica Scandinavica; vol. XLVII, Fasc. I; "Cytological Brush Technique in Malignant Disease of the Endometrium" by J. E. Johnsson and N. G. Stormby; pp. 38–51.

Primary Examiner—Edward M. Coven
Attorney, Agent, or Firm—Roylance, Abrams, Berdo & Goodman

[57] ABSTRACT

Disclosed is a method for obtaining cells from the uterine cervical canal (external os) by inserting a conically tapered brush into the canal and rotating the brush to cause cells to become entrapped by the brush. The brush employed utilizes a spiral wound bristle of 15–20 millimeters in length and of 3 to 7 millimeters in diameter at its widest end. The bristles are formed primarily of a nylon having a maximum diameter of 0.06 millimeters, and relatively soft such as that of a soft toothbrush to more readily bend and avoid damaging in the tissues.

22 Claims, 1 Drawing Sheet

ENDOCERVICAL SAMPLING BRUSH AND SMEAR METHOD

This is a continuation of application Ser. No. 815,766, filed Jan. 2, 1986, now abandoned, which in turn is a continuation of application Ser. No. 614,487, filed May 29, 1984, now abandoned.

BACKGROUND OF THE INVENTION

1. Field of the Invention:

The present invention relates to a method for conducting what is normally referred to as a Pap smear (cytopathologic examination) on females to ultimately examine cells in the endocervical canal for the detection of inflammatory, pre-malignant and malignant changes. Although this invention relates to cytological sampling, it is also excellent for cell sampling from other mucous areas as well as erosions or ulcers of the skin. Also, this invention may be used for microbiological sampling.

The invention also relates to a particular brush employed in a way which significantly increases the cytodiagnostic safety by an increased quantitative and qualitative improvement of the cell yield and therefore, increases the sensitivity of the cellular sample taken. The use of this brush allows the physician to make an early diagnosis of significant cytopathologic abnormalities.

2. Summary of the Prior Art:

Cellular samples for the Pap smear have been taken by several means. One is the utilization of a cotton swab to sample the endocervical canal. Another is the utilization of a wet spatula to sample the exocervix and endocervical canal. Also, a plastic spatula is utilized. Plastic or glass pipettes have been used with an aspiration device. A microcurette instrument has also been developed. In the use of the cotton swab techniques, the difficulty encountered is obtaining sufficient amounts of endocervical cells in the sample for proper evaluation. The aspiration pipettes are awkward and difficult to use. The microcurettes are cost-prohibitive. The wooden spatula, with or without a cotton swab to sample the endocervical canal, is the instrument presently used to obtain a cellular sample for cytopathologic evaluation of the utrine, cervix and vagina (Pap smear). Presently, no simple and practical method has been found that can provide adequate and sufficient cytological epitelium material with an absence of contaminating elements such as leucocytes, sperms, or talcum.

SUMMARY OF THE INVENTION

The present invention is directed to a method for obtaining cells from the uterine cervical canal (external os) by inserting a conically tapered brush into the canal and rotating the brush to cause cells to become entrapped by the brush. The brush employed utilizes a spiral wound bristle of 15-20 millimeters in length and of 3 to 7 millimeters in diameter at its widest end. The bristles are formed primarily of a nylon having a maximum diameter of 0.06 millimeters, and relatively soft such as that of a soft toothbrush to more readily bend and avoid damaging in the tissues.

It is a principal object of the present invention to provide a method and an inexpensive, simple instrument for obtaining endocervical cells in much grater quantities and better quality than, for example, the cotton swab.

A related object of the invention is to increase the number of usable smears obtained by the prior art.

A further related object of the invention is to provide a method for gathering endocervical material which will be better preserved and in greater quantity than that offered by the prior art, particularly cotton swabs.

Yet another object of the present invention is to produce a sample from previously sampled endocervix(ces) with a higher sensitivity and specificity than that of a cotton swab or the other physical devices employed for obtaining smears. This is possible, due to the brushing action in the endocervical canal anatomy.

BRIEF DESCRIPTION OF THE DRAWINGS

Further objects and advantages of the present invention will become apparent as the following description proceeds, taken in conjunction with the accompanying drawings, in which.

DESCRIPTION OF THE METHOD

Figure 1:
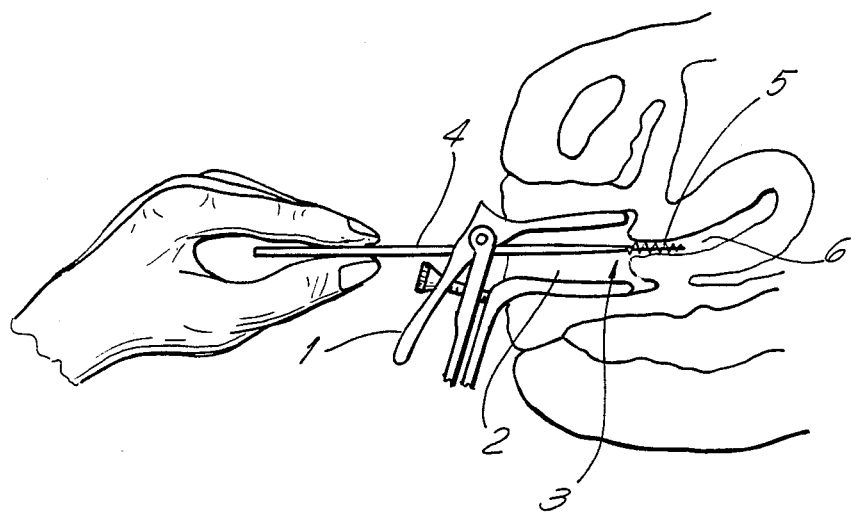
FIG. 1 is a partial transverse sectional view of the female showing the location of the cervical channel, the location of the brush for insertion and rotation.
Figure 2:
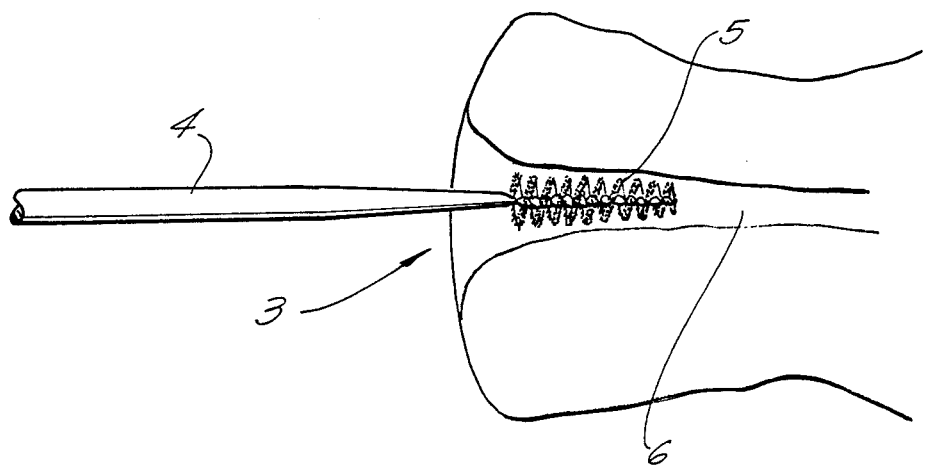
FIG. 2 is a front elevation of the subject brush head illustrating in detail the orientation of the bristles and identifying the configuration.

The method of the present invention is practiced as follows:

The patient is placed as is customary in the normal lithotomy position. As shown in FIG. 1 speculum 1 is inserted into the vagina 2 and opened to view the uterine cervix 3. The brush 4 is advanced with the narrow end of the conically shaped tip 5 entering the endocervical canal 6 until a resistance is felt. The brush 4 is then turned by the operator one-half to two complete turns and then slowly extracted with the mucous and cellular samples within the bristles. This is immediately smeared onto a labeled glass slide by twisting and rolling the brush with pressure onto the slide. Immediately, the smeared slide is "fixed" in alcohol or with a fixitive spray. The brush is then disposed of properly. As to the brush itself, the same has the following dimensional characteristics:

| | |
|---|---|
| Diameter of the shaft | 2.0 millimeters |
| Length of the shaft | 170.0 millimeters |
| Number of bristles | 600 |
| Length of bristles | 5.4 millimeters (top) |
| | 7.5 millimeters (bottom) |
| Diameter of bristles | 0.06 millimeters |

The brush is made of a quality nylon grade, for example DuPont (NC4109HA0025) which is characterized by a tangent modulus (stiffness) of 630,000±260,000 psi, a density of 1.067±0.005 gms/cc, and a moisture at 50% R.H. of about 1.4% and at 100% R.H. of about 3.0%. The plastic shaft is made of polyvinylchloride of N grade 1.2, and the stainless steel of ASIASUS 304, 0.65 millimeters.

Clinical Evaluation

In studies made utilizing the subject brush, and comparing the same to controlled tests, the following is an example in which tabular results can be seen.

EXAMPLE I

Endocervical specimens came from the Section for Early Diagnosis of Cancer of the First Gynecology Service of the Hospital Provincial de Madrid, as well as from the Service of Gynecology (Cytological Laboratory) of the Hospital Insalud in Alicante, and consisted of 276 cases (Table )1. The material is gathered in all of the cases with (1) cotton swabs with a rotating movement once introduced into the endocervix, and (2) the brush with a one-half to two turn movement once introduced into the endoecrvix The conclusions of the study are: (1) the number of usable endocervical smears with the brush is more than three times larger than those done with the cotton swabs. (2) The endocervical material gathered with the brush is better preserved and of greater quantity than the one by the cotton swab. (3) The brush gives a higher specificity than the swabs, statistically significant and with a similar sensitivity. (4) The routine examination of the endocervical canal is insufficient when only relying on a cotton swab for material collection. Therefore, the use of the brush is advisable.

CYTOLOGICAL ENDOCERVICAL TECHNIQUE

| Method of Sampling | Valuable Material | % |
|---|---|---|
| Cotton Swab | 112 | 40.58 |
| Stormby's Brush | 261 | 94.56 |
| Total cases: 276 | | |

Additional reference material may be found in *New Technique for Cytological Sampling With Stormby's Brush*, Ros, E.; Ayala, Mi; Vilplana, E.; Saiz-Pardoy F.; Lorite, L.; Andrade, Mi; Narrow and Rodriguez; Esteban M.; 10th National Cytology Congress, Cadiz, Sept. 29, 30 through Oct. 10, 1983.

EXAMPLE II

Frequency of complications in fifty-seven patients in the use of the brush for sampling of endocervical smears was also studied (see Table below).

TABLE I

| Grade | Pain | Bleeding |
|---|---|---|
| None | 48 | 42 |
| Slight | 7 | 10 |
| Moderate | 2 | 4 |
| Severe | 0 | 0 |
| Total | 57 | 56* |

*1 patient was bleeding already from the ectocervidal smear sample by Ayre's Spatula.

Further reference material may be found in *Cervical Brush For Sampling of Endocervical Smear*, Ahlgren, mats.; Frequency of Complication, Department of Obstetrics and and Gynecology, Lund University Hospital, Lund, Sweden, Nov. 25, 1983.

Although particular embodiments of the invention have been shown and described in full here, there is no intention to thereby limit the invention to the details of such embodiments. On the contrary, the intention is to cover all modifications, alternatives, embodiments, usages and equivalents of the subject invention as fall within the spirit and scope of the invention, specification, and the appended claims.

What is claimed is:

1. A brush assembly for use in connection with cell sampling from the endocervical canal and for smearing the gathered cells onto a glass slide to be used in analysis by the Papanicolaou technique, comprising:
   an elongated handle shaft having opposite ends; and
   an elongated brush directly attached to one of said ends of said handle shaft concentrically with the shaft,
   wherein said brush extends from said one end of the handle shaft over a length ranging from 15 to 20 mm, said brush is cone-shaped and decreases from a major diameter at said one end of the handle shaft ranging from 7.0 to 7.5 mm to a minor diameter ranging from 3.0 to 5.4 mm, and said brush comprises approximately 600 flexible bristles made of nylon, each of said bristles having a diameter of approximately 0.06 mm and a stiffness characterized by a tangent modulus of $630,000 \pm 260,000$ psi.

2. A method of obtaining and analyzing endocervical cellular samples comprising the steps of
   providing a brush assembly comprising an elongated handle shaft, and an elongated brush directly attached to one end of said handle shaft concentrically with the shaft, said brush extending from said one end of the shaft over a length ranging from 15 to 20 mm, the brush being cone-shaped and decreasing from a major diameter at said one end of the handle shaft ranging from 7 to 7.5 mm to a minor diameter ranging from 3 to 5.4 mm, and the brush comprising approximately 600 flexible bristles made of nylon, each of the bristles having a diameter of approximately 0.06 mm,
   inserting the brush into the endocervical canal until the lower part of the brush is just inside the canal,
   rotating the brush assembly, thereby entrapping cells in the interstices between the bristles,
   removing the brush from the endocervical canal,
   smearing the entrapped, but by the hydrophobic properties of the nylon bristles easily detached, cells from the brush onto a glass slide by twisting and rolling the brush with pressure onto the slide,
   fixing the smeared cells to the glass slide, and analyzing the glass slide thus prepared by the Papanicolaou technique.

3. A brush assembly for use in connection with cell sampling from the endocervical canal and for smearing the gathered cells onto a glass slide to be used in cellular analysis for the detection of disease, the combination comprising:
   an elongated handle shaft having opposite ends; and
   an elongated brush attached to one of said ends of said handle shaft,
   wherein said brush extends from said one end of the handle shaft over a length ranging from approximately 15 to 20 mm, said brush is cone-shaped and decreases from a major diameter at said one end of the handle shaft ranging from approximately 7.0 to 7.5 mm to a minor diameter at the distal end ranging from approximately 3.0 to 5.4 mm, and said brush comprises approximately 600 flexible bristles made of nylon, each of said bristles having a diameter of approximately 0.06 mm and a stiffness characterized by a tangent modulus of $630,000 \pm 260,000$ psi.

4. A brush assembly according to claim 3, wherein said cone-shape tapers substantially uniformly from said major diameter to said minor diameter at said distal end.

5. A method of obtaining and analyzing endocervical cellular samples comprising the steps of
   providing a brush assembly comprising an elongated handle shaft, and an elongated brush attached to one end of said handle shaft, said brush extending from said one end of the shaft over a length ranging from approximately 15 to 20 mm, the brush being cone-shaped and decreasing from a major diameter at said one end of the handle shaft ranging from approximately 7.0 to 7.5 mm to a minor diameter at the distal end ranging from approximately 3.0 to 5.4 mm, and the brush comprising approximately 600 flexible bristles made of nylon, each of the bristles having a diameter of approximately 0.06 mm, inserting the brush into the endocervical canal until the part adjacent the distal end of the brush is just inside the canal, rotating the brush assembly, thereby entrapping cells in the interstices between the bristles, removing the brush from the endocervical canal, smearing the entrapped, but by the hydrophobic properties of the nylon bristles easily detached, cells from the brush onto a glass slide by twisting and rolling the brush with pressure onto the slide, fixing the smeared cells to the glass slide, and analyzing the glass slide thus prepared.

6. A method according to claim 5, wherein said cone-shape tapers substantially uniformly from said major diameter to said minor diameter at said distal end.

7. A method according to claim 5, wherein said bristles have a stiffness characterized by a tangent modulus of 630,000±260,000 psi.

8. A brush assembly for use in connection with cell sampling from the endocervical canal and for smearing the gathered cells onto a glass slide to be used in cellular analysis for the detection of disease, the combination comprising:

an elongated handle shaft having opposite ends; and an elongated brush attached to one of said ends of said handle shaft, wherein said brush extends from said one end of the handle shaft over a length ranging from approximately 15 to 20 mm, said brush is cone-shaped and decreases from a major diameter at said one end of the handle shaft which is a maximum of approximately 7.5 mm to a minor diameter at the distal end which is a maximum of approximately 5.4 mm, and said brush comprises approximately 600 flexible bristles made of a hydrophobic material, each of said bristles having a diameter of approximately 0.06 mm and a stiffness characterized by a tangent modulus of 630,000±260,000 psi.

9. A brush assembly according to claim 8, wherein said cone-shape tapers substantially uniformly from said major diameter to said minor diameter at said distal end.

10. A brush assembly according to claim 8, wherein said hydrophobic material is nylon.

11. A method of obtaining and analyzing endocervical cellular samples comprising the steps of providing a brush assembly comprising an elongated handle shaft, and an elongated brush attached to one end of said handle shaft, said brush extending from said one end of the shaft over a length ranging from approximately 15 to 20 mm, the brush being cone-shaped and decreasing from a major diameter at said one end of the handle shaft which is a maximum of approximately 7.5 mm to a minor diameter at the distal end which is a maximum of approximately 5.4 mm, and the brush comprising approximately 600 flexible bristles made of a hydrophobic material, each of the bristles having a diameter of approximately 0.06 mm, inserting the brush into the endocervical canal until the part adjacent the distal end of the brush is just inside the canal, rotating the brush assembly, thereby entrapping cells in the interstices between the bristles, removing the brush from the endocervical canal, smearing the entrapped, but by the hydrophobic properties of the flexible bristles easily detached, cells from the brush onto a glass slide by twisting and rolling the brush with pressure onto the slide, fixing the smeared cells to the glass slide, and analyzing the glass slide thus prepared.

12. A method according to claim 11, wherein said cone-shape tapers substantially uniformly from said major diameter to said minor diameter at said distal end.

13. A method according to claim 11, wherein said hydrophobic material is nylon.

14. A method according to claim 11, wherein said bristles have a stiffness characterized by a tangent modulus of 630,000±260,000 psi.

15. A method of obtaining and analyzing endocervical cellular samples comprising the steps of providing a brush assembly comprising an elongated handle shaft, and an elongated brush attached to one end of said handle shaft, said brush extending from said one end of the shaft over a length ranging from 15 to 20 mm, the brush being cone-shaped and decreasing from a major diameter at said one end of the handle shaft ranging from 7.0 to 7.5 mm to a minor diameter at the distal end ranging from 3.0 to 5.4 mm, and the brush comprising approximately 600 flexible bristles made of a hydrophobic material, each of the bristles having a diameter of approximately 0.06 mm, inserting the brush into the endocervical canal until the part adjacent the distal end of the brush is just inside the canal, rotating the brush assembly, thereby entrapping cells in the interstices between the bristles, removing the brush from the endocervical canal, separating the entrapped, but by the hydrophobic properties of the flexible bristles easily detached, cells from the brush, and analyzing the cells thus separated.

16. A method according to claim 15, wherein said bristles have a stiffness characterized by a tangent modulus of 630,000±260,000 psi.

17. A method according to claim 15, wherein said cone-shape tapers substantially uniformly from said major diameter to said minor diameter at said distal end.

18. A method according to claim 15, wherein said hydrophobic material is nylon.

19. A method of obtaining and analyzing endocervical cellular samples comprising the steps of providing a brush assembly comprising an elongated handle shaft, and an elongated brush attached to one end of said handle shaft, said brush extending from said one end of the shaft over a length ranging from approximately 15 to 20 mm, the brush being cone-shaped and decreasing from a major diameter at said one end of the handle shaft ranging from approximately 7.0 to 7.5 mm to a minor diameter at the distal end ranging from approximately 3.0 to 5.4 mm, and the brush comprising approximately 600 flexible bristles made of a hydrophobic material, each of the bristles having a diameter of approximately 0.06 mm.

inserting the brush into the endocervical canal until the part adjacent the distal end of the brush is just inside the canal, rotating the brush assembly, thereby entrapping cells in the interstices between the bristles, removing the brush from the endocervical canal, separating the entrapped, but by the hydrophobic properties of the flexible bristles easily detached, cells from the brush, and analyzing the cells thus separated.

20. A method according to claim 19, wherein said bristles have a stiffness characterized by a tangent modulus of 630,000±260,000 psi.

21. A method according to claim 19, wherein said cone-shape tapers substantially uniformly from said major diameter to said minor diameter at said distal end.

22. A method according to claim 19, wherein said hydrophobic material is nylon.

* * * * *